(12) United States Patent
Knusel et al.

(10) Patent No.: US 6,300,327 B1
(45) Date of Patent: *Oct. 9, 2001

(54) COMPOSITIONS AND METHODS FOR POTENTIATION OF NEUROTROPHIN ACTIVITY

(75) Inventors: Beat J. Knusel, Los Angeles; Franz F. Hefti, Altadena, both of CA (US)

(73) Assignee: The University of Southern California, Los Angeles, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/795,967

(22) Filed: Feb. 6, 1997

Related U.S. Application Data (63) Continuation of application No. 08/410,584, filed on Mar. 27, 1995, now abandoned, which is a continuation of application No. 08/091,078, filed on Jul. 13, 1993, now abandoned, which is a continuation of application No. 07/789,715, filed on Nov. 8, 1991, now abandoned.

(51) Int. Cl.$^7$ .................. A61K 31/395; A61K 31/55; A61K 31/66
(52) U.S. Cl. .................. 514/211; 514/210; 514/22; 514/122; 435/169
(58) Field of Search ............. 514/22, 211, 210; 424/122; 435/169

(56) References Cited

U.S. PATENT DOCUMENTS

| | | | |
|---|---|---|---|
| 3,731,683 | 5/1973 | Zaffaroni | 7/2 |
| 3,797,494 | 3/1974 | Zaffaroni | 15/6 |
| 4,336,243 | 6/1982 | Sanvordeker et al. | 15/3 |
| 4,555,402 | 11/1985 | Matsuda et al. | 35/74 |
| 4,877,776 | 10/1989 | Murakata et al. | 31/71 |
| 4,923,986 | 5/1990 | Murakata et al. | . |
| 5,516,772 * | 5/1996 | Glicksman et al. | 514/211 |

FOREIGN PATENT DOCUMENTS

| | | |
|---|---|---|
| 0 303 697 A1 | 3/1987 | (EP) . |
| 0 323 171 A2 | 12/1988 | (EP) . |
| 0 410 697 | 1/1991 | (EP) . |

OTHER PUBLICATIONS

Barde, Y.A., "Trophic Factors and Neuronal Survival", *Neuron* 2:1525–1534 (1989).
Thoenen, H., "The Changing Scene of Neurotrophic Factors", *Trends Neorsci.* 14:165–170 (1991).
Leibrock, J. et al., "Molecular Cloning and Expression of Brain–Derived Neurotrophic Factor", *Nature* 341:149–152 (1989).
Ernfors, P. et al., "Identification of Cells in Rat Brain and Peripheral Tissues Expressing mRNA for Members of the Nerve Growth Factor Family", *Neuron* 5:511–526 (1990).
Hohn, A. et al., "Identification and Characterization of a Novel Member of the Nerve Growth Factor/Brain–Derived Neurotrophic Factor Family", *Nature* 344: 339–341 (1990).
Maisonpierre, P.C. et al., "Neurotrophic–3, A Neurotrophic Factor Related to NGF and BDNF" *Science* 247: 1446–1451 (1990).
Jones, K.R. aqnd Reichardt, L.F., "Molecular Cloning of a Human Gene that is a Member of the Nerve Growth Factor Family", *Proc. Natl. Acad. Sci. USA* 87: 8060–8064 (1990).
Hallbrook, F. et al., "Evolutionary Studies on the Nerve Growth Factor Family Reveal a Novel Member Abundantly Expressed in Xenopus Ovary", *Neuron* 6: 845–858 (1991).
Berkemeier, L.R. et al., "Neurotrophin–5: A Novel Neurotrophic Factor That Activates trk and trkB" *Neuron* 6:845–858 (1991).
Hefti, F. et al., "Function of Neurotrophic Factors in the Adult and Aging Brain and Their Possible Use in the Treatment of Neurodegenerative Diseases", *Neurobiol. Aging* 10:515–533 (1989).
Snider, W.D. and Johnson, Jr., E.M., "Neurotrophic Molecules" *Annals of Neurology* 26:489–506 (1989).
Appel, S.H., "A Unifying Hypothesis for the Cause of Amyotrophic Lateral Sclerosis, Parkinsonism, and Alzheimer's Disease" *Ann. Neurol.* 10:499–505 (1981).
Chao, M.V. et al., "Gene Transfer and Molecular Cloning of the Human NGF Receptor" *Science* 232:518–521 (1986).
Radeke, M.J. et al., "Gene Transfer and Molecular Cloning of the Rat Nerve Growth Factor Receptor: A New Class of Receptors" *Nature* 325:593–597 (1987).
Hemptstead, B.L. et al., "High–affinity NGF Binding Requires Coexpression of the trk Proto–Oncogene and the Low–affinity NGF Receptor" *Nature* 344:339–341 (1990).
Nakanishi, S. et al., "K–252a, a Novel Microbial Product, Inhibits Smooth Muscle Myosin Light Chain Kinase", *J. Biol. Chem.* 263:6215–6219 (1986).
Kase, H. et al., "K–252 Compounds, Novel and Potent Inhibitors of Protein Kinase C and Cyclic Nucleotide–dependent Protein Kinases" *Biochem. Biophys. Res. Commun.* 142:436–440 (1987).
Koizumi, S. et al., "K–252a: A Specific Inhibitor of the Action of Nerve Growth Factor on PC12 Cells", *J. Neurosci.* 8:715–721 (1988).

(List continued on next page.)

*Primary Examiner*—Theodore J. Criares
(74) *Attorney, Agent, or Firm*—Fulbright & Jaworski L.L.P.

(57) ABSTRACT

Compositions and methods for use in modulating neurotrophin activity, wherein the active agent is at least one compound which potentiates neurotrophin activity. A preferred class of active agents is K-252 compounds, including both microbial metabolites and derivatives thereof. Neurotropin activity is modulated by administration of an effective amount of at least one compound which potentiates neurotrophin activity. Potentiation of NT-3 by K-252b, K-252a, KT5720, and KT5823 provides a model for therapeutic intervention in a variety of neuropathological conditions.

10 Claims, 5 Drawing Sheets

OTHER PUBLICATIONS

Matsuda, Y. and Fukuda, J., "Inhibition by K–252a, a New Inhibitor of Protein Kinase, of Nerve Growth Factor–induced Neurite Outgrowth of Chick Embryo Dorsal Root Ganglion Cells", *Neurosci. Lett.* 87:295–301 (1989).

B. Knusel et al., "K–252 Compounds: Modulators of Neurotrophin Signal Transduction", *J. NeuroChemistry*, 59: No. 6, pp. 1987–1966 (Dec. 1992).

B. Knusel et al., "K–252b Selectively Potentiates Cellular Actions and trk Tyrosine Phosphorylation Mediated by Neurotrophin–3", *J. NeuroChemistry*, 59: No. 2, pp. 715–722 (Aug. 1992).

K. Abe et al., "Arachidonic Acid Metabolism in Ischemic Neuronal Damage", *Annals of the N.Y. Academy of Sci.*, 559:259–268 (1989).

M. Yoshidomi et al., "Inhibition of Protein Kinase Activities Ameliorates Postischemic Brain Cell Damage", *J. Cerebral Blood Flow and Metabolism*, 9:S186 (1989).

G.D. Borasio, "Diffeerential Effects of the Protein Kinase Inhibitor K–252a on the In Vitro Survival of Chick Embryonic Neurons", *Neuroscience Letters*, 108:No. 1, 2, pp. 207–212 (1990).

B. Knusel et al., "K–252b Is a Selective and Nontoxid Inhibitor of Nerve Growth Factor Action on Cultured Brain Neurons", *J. Neurochem.*, 57:No. 3, pp. 955–962 (1991).

S. Koiaumi et al., "K–252a: A Specific Inhibitor of the Action of Nerve Growth Factor on PC12 Cells", *J. Neurosci.*, 8:No. 2, pp. 715–721 (1988).

Olson et al., "Nerve Growth Factor Affects C–Nicotine Binding, Blood Flow, EEG, and Verbal Episodic Memory in an Alzheimer Patient", *J. Neural Trans.* 4:79–95 (1992).

Olson et al., "Intraputaminal Infusion of Nerve Growth Factor to Support Adrenal Medullary Autografts in Parkinson's Disease", *Arch Neurol.* 48:373–381 (Apr. 1991).

Matsuda et al., "Nerve Growth Factor Promotes Human Hemopoietic Colony Growth and Differentiation", *Proc. Natl. Acad. Sci. USA* 85:6508–6512 (Sep. 1988).

Apfel et al., "Nerve Growth Factor Prevents Experimental Cisplatin Neuropathy", *Ann. Neurol.* 31:76–80 (1992).

Parvinen et al., "Expression of β–Nerve Growth Factor and Its Receptor in Rat Seminiferous Epithelium: Specific Function at the Onset of Meiosis", *J.Cell Biol.* vol. 117, No. 3, pp. 629–641 (May, 1992).

Williams, Lawrence R., "Hypophagia Is Induced By Intracerebroventricular Administration of Nerve Growth Factor", *Experimental Neurology* 113:31–37 (1991).

Lapchak, Paul A. and Hefti, Franz, "BDNF and NGF Treatment in Leioned Rats: Effects on Cholinergic Function and Weight Gain", *Molecular Neuroscience*, NeuroReport 3, 405–408 (1992).

Berkemeier et al., "Neurotrophin–5: A Novel Neurotrophic Factor That Activates trk and trkB", *Neuron* 7:857–866 (Nov. 1991).

Ip et al., "Mammalian Neurotrophin–4: Structure, Chromosomal Localization, Tissue Distribution, and Receptor Specificity", *Proc. Natl. Acad. Sci. USA*, 89:3060–3064 (Apr. 1992).

Lamballe et al., "trkC, and New Member of the trk Family of Tyrosine Protein Kinases, is a Receptor for Neurotrophin–3", *Cell* 66:967–979 (Sep. 6, 1991).

Cordon–Cardo et al., "The trk Tyrosine Protein Kinase Mediates the Mitogenic Properties of Nerve Growth Factor and Neurotrophin–3", *Cell* 66:173–183 (Jul. 12, 1991).

Soppet et al., "The Neurotrophic Factors Brain–Derived Neurotrophic Factor and Neurotrophin–3 Are Ligands for the trkB Tyrosine Kinase Receptor", *Cell* 65:895–903 (May 31, 1991).

Squinto et al., "trkB Encodes a Functional Receptor for Brain–Derived Neurotrophic Factor and Neurotrophin–3 but Not Nerve Growth Factor", *Cell* 65:885–893 (May 31, 1991).

Nikodijevic et al., "Nerve Growth Factor and K–252a Increase Catecholamine Release from PC12 Cells", *J. Neuroscience Research* 26:288–295 (1990).

Apfel et al., "Nerve Growth Factor Prevents Toxic Neuropathy in Mice", *Annals of Neurology*, 29:87–89 (Jan., 1991).

Sano, M. et al., "A Nerve Growth Factor–dependent Protein Kinase That Phosphorylates Microtubule–associated Proteins in Vitro: Possible Involvement of its Activity in the Outgrowth of Neurites from PC12 Cells", *J. Neurochem.* 55:427–435 (1990).

Knusel, B. et al., "Trophic Actions of Recombinant Human Nerve Growth Factor on Cultured Rat Embryonic CNS Cells", *Experimental Neurology* 110:274–383 (1990).

Knusel et al., "Selective and Nonselective Stimulation of Central Cholinergic and Dopaminergic Development in Vitro by Nerve Growth Factor, Basic Fibroblast Growth Factor, Epidermal Growth Factor, Insulin and the Insulin––like Growth Factors I and II", *J. Neurosci.* 10:558–570 (1990).

Rosenthal, A. et al., "Primary Structure and Biological Activity of a Novel Human Neurotrophic Factor", *Neuron* 4:767–773 (1990).

Kaplan, D.R. et al., "PDGF Beta Receptor Stimulates Tyrosine Phosphorylation of GAP and Association of GAP with a Signaling Complex", *Cell* 61:125–133 (1990).

Vetter, M.L. et al., "Nerve Growth Factor Rapidly Stimulates Tyrosine Phosphorylation of Phospholipase C–gamma1 by a Kinase Activity Associated with the Product of trk Protooncogene", *Proc. Natl. Acad. Sci. USA* 88:5650–5654 (1991).

Hashimoto, S., "K–252a, A Potent Protein Kinase Inhibitor, Blocks Nerve Growth Factor–induced Neurite Outgrowth and Changes in the Phosphorylation of Proteins in PC12h Cells", *J. Cell. Biol.* 107:1531–1539 (1988).

Widmer, Hans R. et al., "Stimulation of Phosphatidylinositol Hydrolysis by Brain–Derived Neurotrophic Factor and Neurotrophin–3 in Rat Cerebral Cortical Neurons Developing in Culture", *J. of Nuerochem.*, vol. 59, No. 6, pp. 2113–2124 (1992).

Merlio, J. P. et al., Molecular Cloning of Rat trkC and Distribution of Cells Expressing Messenger RNAs for Members of the trkFamily in the Rat Central Nervous System:, *Neuroscience*, vol. 51, No. 3, pp. 513–532 (1992).

Altar, C. Anthony et al., "Characterization and Topography of High–Affinity $^{125}$I–Neurotrophin–3 Binding to Mammalian Brain", *J. of Neuroscience*, 13(2):733–732 (Feb. 1993).

Takeda, Atsushi et al., "Decreased expression of Neurotrophin–3 mRNA in the Rat Hippocampus Following Transient Borebrain Ischemia", *Brain Research*, 569:177–180 (1992).

* cited by examiner

FIG. 5

COMPOSITIONS AND METHODS FOR POTENTIATION OF NEUROTROPHIN ACTIVITY

This application is a file wrapper continuation of U.S. patent application Ser. No. 08/410,584, filed on Mar. 27, 1995, now abandoned, which is a continuation of Ser. No. 08/091,078, filed Jul. 13, 1993, now abandoned, which is a continuation of Ser. No. 07/789,715, filed Nov. 8, 1991, now abandoned.

STATEMENT REGARDING FEDERALLY SPONSORED RESEARCH OR DEVELOPMENT

This invention was made with Government support under Contract No. 9021255, awarded by the National Science Foundation. The Government has certain rights in this invention.

BACKGROUND OF THE INVENTION

The present invention relates to compositions which are useful in potentiating neurotrophin activity, as well as methods for the preparation and use thereof.

Protein growth factors of the neurotrophin family, which includes nerve growth factor (NGF), brain-derived neurotrophic factor (BDNF), neurotrophin-3 (NT-3), neurotrophin-4 (NT-4) and neurotrophin-5 (NT-5) regulate nervous system development [Barde, Y-A., "Trophic factors and neuronal survival," Neuron 2:1525–1534 (1989); Thoenen, H., "The changing scene of neurotrophic factors," Trends Neurosci 14:165–170 (1991); Leibrock, J. et al., "Molecular cloning and expression of brain-derived neurotrophic factor," Nature 341:149–152 (1989); Ernfors, P. et al., "Identification of cells in rat brain and peripheral tissues expressing mRNA for members of the nerve growth factor family," Neuron 5:511–526 (1990); Hohn, A. et al., "Identification and characterization of a novel member of the nerve growth factor/brain-derived neurotrophic factor family," Nature 344:339–341 (1990); Maisonpierre, P. C. et al., "Neurotrophin-3: a neurotrophic factor related to NGF and BDNF," Science 247:1446–1451 (1990); Rosenthal, A. et al., "Primary Structure and Biological Activity of a Novel Human Neurotrophic Factor," Neuron 4:767–773 (1990); Jones, K. R. and Reichardt, L. F., "Molecular cloning of a human gene that is a member of the nerve growth factor family", Proc. Natl. Acad. Sci. USA 87:8060–8064 (1990); Hallbook, F. et al., "Evolutionary studies on the nerve growth factor family reveal a novel member abundantly expressed in Xenopus ovary," Neuron 6:845–858 (1991); Berkemeier, L. R. et al., "Neurotrophin-5: a novel neurotrophic factor that activates trk and trkB," Neuron (in press)]. In addition, the neurotrophins are strongly implicated as playing an important role in structural maintenance, plasticity and repair of the adult nervous system [Hefti, F. et al., "Function of neurotrophic factors in the adult and aging brain and their possible use in the treatment of neurodegenerative diseases," Neurobiol. Aging 10:515–533 (1989)].

Neurobiological research carried out in recent years has confirmed that development, maintenance of function and regeneration of neurons is profoundly influenced by the neurotrophic factors. These neurotrophins stimulate mechanisms necessary for survival, neurite growth and functions related to transmitter production and release. For example, it has long been known that nerve growth factor (NGF), the first and best characterized neurotrophin, is a neurotrophic factor for peripheral sympathetic and sensory neurons, and more recent findings show that NGF also affects cholinergic neurons in the brain. NGF is required by sympathetic and dorsal root ganglion cells for survival during embryonic and early postnatal life, and is also critical to the normal function of these neuronal types in adult animals. NGF is further implicated in the regulation of a variety of developmental processes such as naturally-occurring cell death, differentiation, process outgrowth and synaptic rearrangement.

Experiments over the last few decades have yielded evidence that NGF regulates a variety of cellular processes important for neuronal function. Administration of pharmacological doses of NGF to rodents results in striking increases in ganglion cell size, axonal branching in the periphery and dendritic arborization as demonstrated by, e.g., intracellular staining techniques. Furthermore, administration of NGF leads to increases in the synthesis of transmitter enzymes and increases in the synthesis of peptides in dorsal root ganglion cells. NGF also exerts effects on preganglionic neurons innervating sympathetic ganglion cells, presumably an indirect effect of its influence on the ganglion cells. Importantly, NGF can prevent death of responsive neurons pursuant to mechanical, chemical and immunological insults. When NGF deprivation is induced by axotomy or administration of antisera, atrophy and reduction in the synthesis of transmitter enzymes occur. Furthermore, when autoimmunity to NGF is induced in rats, guinea pigs and rabbits, there is massive death of sympathetic ganglion cells over a period of several months in animals that generate high antibody titers. Finally, even in adulthood, several neuronal populations in the peripheral and central nervous system respond to transection of their axons by atrophy, reductions in transmitter synthesis and significant degrees of cell death. Taken together, all of these finding in vivo suggest that trophic factors act chronically in the mature animal to maintain normal function. Therefore, trophic deficiency is probably an important mechanism in disease states of adulthood [see Snider, W. D. and Johnson, Jr., E. M., "Neurotrophic Molecules," Annals of Neurology 26:489–506 (1989) and references cited therein].

Other neurotrophic molecules characterized thus far influence various other neuronal populations. The existence of different patterns of specificity suggests that there may be a multitude of neurotrophins with different specificities and activities. As the molecules occur in minimal quantities, their isolation is a cumbersome and time-consuming effort.

The discovery of neurotrophic factors has obvious implications with respect to neurodegenerative diseases. Indeed, it has been hypothesized that the lack of neurotrophic factors is responsible for the degeneration of selective neuronal populations as it occurs in Parkinson's disease, Alzheimer's disease and amyotrophic lateral sclerosis, and that application of corresponding neurotrophic factor might prevent neuronal degeneration [Appel, S. H., "A unifying hypothesis for the cause of amyotrophic lateral sclerosis, parkinsonism, and Alzheimer's disease," Ann. Neurol. 10:499–505 (1981)]. In particular, as NGF is a trophic factor for the population of basal forebrain cholinergic neurons which degenerates in Alzheimer's disease, it has been speculated that NGF may be useful in the treatment of this disease.

Classical neuropharmacology attempts to influence mechanisms related to neuronal impulse flow and transmission at the synapse. Currently-used drugs and available pharmacological tools do not affect the structural features of the central nervous system. Moreover, there is a lack of compounds that are able to promote regeneration, plasticity and maintenance of structural integrity of selected neuronal systems. An increased understanding of the properties of neurotrophic factors is virtually certain to lead to the development of a new, structurally-oriented neuropharmacology. In particular, neurotrophic factors shall undoubtedly prove useful in the treatment of neurodegenerative diseases associated with structural disintegration of selected neuronal systems of brain areas.

One of the more exciting features of neurotrophic molecules from a clinical standpoint is their ability to promote cell survival after a variety of insults. For example, it has been shown that NGF has the ability to save neurons that would ordinarily die after mechanical injury. These injuries have been most commonly produced by transecting the axons of sympathetic and dorsal root ganglion cells or basal cholinergic forebrain neurons. Such injuries separate the soma from contact with targets and presumably cause neurons to degenerate because of loss of trophic support, although other mechanisms may be involved. In every circumstance in which axons of a responsive neuronal population have been transected, NGF has saved at least some neurons from degenerating. NGF works after systemic administration for peripheral neurons, as well as after local application to axon tips, and is effective after intraventricular administration for neurons within the central nervous system. Another neurotrophic molecule, FGF, is also effective in some of these same paradigms. This ability to prevent cell death after injury is obviously relevant to the problem of promoting neural regeneration [see Snider and Johnson, supra, at 498 et seq.].

Neurotrophins have also been shown to save neurons after exposure to certain toxins. For example, the concomitant administration of NGF with 6-hydroxydopamine (which is presumed to act by destroying sympathetic nerve terminals, thereby interfering with the uptake of NGF from a target) can completely prevent the death of cells that occurs upon administration in early postnatal life. In addition, NGF has been shown to save neurons after administration of vinblastine and coichicine, which inhibit axoplasmic transport. Further, NGF can partially prevent the cell death in dorsal root ganglia caused by administration of the sensory toxin capsaicin to newborn animals.

Neurotrophins are also implicated in a number of different ways with an organism's maintenance of healthy neuronal function. For example, NGF has been shown to suppress primary infection of dorsal root and sympathetic ganglion cells by herpes simplex type I virus; NGF is believed to suppress the expression of gene products necessary for viral replication. In addition, lymphocytic infiltration and destruction of sympathetic ganglia induced by administration of guanethidine and its analogues (resulting in autoimmune attack) is completely prevented by concomitant administration of NGF. The presumed mode of action is by suppressing the expression of the antigen on the ganglion cell surface, leading to the suggestion that another physiological role of trophic factors in adult animals may be to maintain immunological silence of irreplaceable neurons [Snider et al., supra, at 499].

Unfortunately, several formidable obstacles remain to be overcome before neurotrophic peptides can be of widespread clinical utility. First, sufficient quantities of the neurotrophins must be available; recombinant DNA technology will be required to engineer expression vectors that produce large quantities of biologically active factors. Further, the practical difficulties of and limitations on the administration and delivery of such molecules must be overcome. In order to be able to reach neuronal populations in the brain, neurotrophic factors would have to be given intracerebrally, as these proteins do not cross the blood-brain barrier. In human patients in particular, there would only be limited options for administration of neurotrophins per se. Neurotrophic factors purified from natural sources or produced by recombinant techniques could potentially be chronically infused into the brain with the help of mechanical pump devices; however, subcutaneous pumps are relatively complex devices necessitating surgical intervention, and stability of the active proteins during storage in these pump devices would be expected to necessitate special preparations. It is encouraging that local administration of NGF to the distal parts of injured neurons enhances survival and regeneration, thus suggesting the potential in some situations for local administration; nonetheless, even in those instances, the use of some sort of prosthetic device appears necessary. An alternative method of administration would involve the use of slow-release intracerebral implants containing the active protein embedded in a biodegradable polymer matrix. At this time, existing polymers provide stable release rates of only several weeks.

While administration of modified neurotrophin molecules or active fragments thereof may ultimately provide a solution to the problem of providing therapeutic agents with neurotrophic activities, at this time very little is known about the possibility of producing active fragments of neurotrophic factors. Accordingly, it has been suggested that perhaps the best long-range hope for this class of agents lies in understanding in detail their interaction with their receptors and the molecular mechanisms of their trophic and survival-promoting actions; this may allow the design and use of low-molecular-weight drugs that mimic the effects of trophic factors and that can be administered in more traditional and practical ways [Snider, supra, at 499]. The identification of agents that modify components of neurotrophin activity is in and of itself a valuable contribution to the art, in view of the substantial present utility of such agents in obtaining a clearer understanding of the molecular mechanisms involved and in the design of novel therapeutic agents.

At least two types of proteins are apparently involved in the formation of functional receptors for neurotrophin growth factors. These are the low affinity NGF receptor protein (p75-NGFR) [Chao, M. V. et al., "Gene transfer and molecular cloning of the human NGF receptor", *Science* 232:518–521 (1986); Radeke, M. J., et al., "Gene transfer and molecular cloning of the rat nerve growth factor receptor: a new class of receptors"; *Nature* 325:593–597 (1987)] and products of trk-related proto-oncogenes [Hempstead, B. L. et al., "High-affinity NGF binding requires coexpression of the trk proto-oncogene and the low-affinity NGF receptor," *Nature* 344:339–341 (1990)]. The trk gene products, but not the p75-NGFR, exhibit protein kinase activity. Individual trk receptors bind to and stimulate tyrosine phosphorylation of different subsets of neurotrophins. Trk binds to NGF but not BDNF, trkB binds BDNF but not NGF. NT-3 is capable of interacting with trk and trkB receptors and with trkC. The interaction of NT-3 with multiple trk receptors may allow this factor to control the survival of populations of neurons expressing different trk gene products.

U.S. Pat. No. 4,555,402 to Matsuda et al., the entire disclosure of which is hereby incorporated by reference, discloses the isolation of a physiologically-active substance denominated as K-252. This compound is described as having antiallergic and antihistamine-releasing activities.

U.S. Pat. No. 4,923,986 to Murakata et al., the entire disclosure of which is also hereby incorporated by reference, discloses a class of derivatives of K-252 represented by the general formula wherein $W_1$, $W_2$, $R^1$, $R^2$, $R^3$, $R^4$, X and Y represent various substituents. The compounds are physiologically active substances that inhibit protein kinase C and exhibit an antitumor activity.

U.S. Pat. No. 4,877,776 to Murakata et al., the entire disclosure of which is also hereby incorporated by reference, discloses another class of derivatives of K-252 represented by the general formula wherein $R^1$ and $R^2$ are independently H or OH, X represents COOH, COOR or $CH_2OH$; Y represents H, R or COR; and Z represents OH, OR or SR, in which R represents lower alky. These derivatives are described as exhibiting C-kinase inhibitory activity, and were expected to be useful as an active ingredient of antitumor agents, etc.

Of the compounds disclosed in the aforementioned U.S. patents, two have been known for the longest time and have in particular become the subjects of substantial research scrutiny. K-252a and K-252b, two related alkaloid-like compounds from microbial origin known to interfere with protein kinase activities in cell-free systems, have been found to inhibit several biological actions of NGF [Nakanishi, S. et al., "K-252a, a novel microbial product, inhibits smooth muscle myosin light chain kinase," *J. Biol. Chem.* 263:6215–6219 (1986); Kase, H. et al., "K-252 compounds, novel and potent inhibitors of protein kinase C and cyclic nucleotide-dependent protein kinases," *Biochem. Biophys. Res. Commun.* 142:436440 (1987); Koizumi, S. et al., "K-252a: a specific inhibitor of the action of nerve growth factor on PC12 cells," *J. Neurosci.* 8:715–721 (1988); Matsuda, Y. and Fukuda, J., "Inhibition by K-252a, a new inhibitor of protein kinase, of nerve growth factor-induced neurite outgrowth of chick embryo dorsal root ganglion cells," *Neurosci. Lett.* 87:295–301 (1989)]. K-252a prevents the NGF induced morphological transformation of proliferating PC12 pheochromocytoma cells into neuron-like cells and inhibits the NGF stimulated, but not the basic fibroblast growth factor (bFGF) or epidermal growth factor (EGF) stimulated phosphorylation of selected proteins [Hashimoto, S., "K-252a, a potent protein kinase inhibitor, blocks nerve growth factor-induced neurite outgrowth and changes in the phosphorylation of proteins in PC12h cells," *J. Cell. Biol.* 107:1531–1539 (1988); Sano, M. et al., "A nerve growth factor-dependent protein kinase that phosphorylates microtubule-associated proteins in vitro: possible involvement of its activity in the outgrowth of neurites from PC12 cells," *J. Neurochem.* 55:427–435 (1990)]. Thus, to date compounds as described in the aforementioned U.S. patents have been shown to have only an inhibitory affect on neurotrophin activity.

The development of non-peptide agonistic molecules for neurotrophic factors which pass the blood-brain barrier, while acknowledged as theoretically possible, has heretofore been considered potentially to prove a herculean task [Hefti, F. et al. (1989), supra, at 525]. It would therefore be highly desirable to identify low-molecular-weight agents which modulate (and, most desirably, potentiate) neurotrophin activity, both for purposes of elucidating the molecular mechanisms of neurotrophin action and as useful therapeutic agents for treatment of, e.g., neurodegenerative diseases.

It is an object of the present invention to provide compositions for use in potentiation of neurotrophin activity, as well as methods for the preparation and use thereof.

SUMMARY OF THE INVENTION

In accordance with the present invention, there are provided compositions and methods for use in the potentiation of neurotrophin activity. Pursuant to one aspect of the present invention, the compositions comprise an effective amount of at least one K-252 compound, as hereinafter defined. One preferred class of such compounds is represented by general formula I in which $W_1$, $W_2$, $R^1$, $R^2$, $R^3$, $R^4$, X and Y are as hereinafter defined. In particular, selective potentiation of the activity of neurotrophin-3 (NT-3) has been demonstrated using particularly preferred compounds of general formula I in which $W_1$, $W_2$, $R^1$, $R^2$, $R^3$ and $R^4$ are all hydrogen, Y is OH and X is -COOCH₃ (K-252a) or —COOH (K-252b). In accordance with another aspect of the invention, neurotrophin activity is modulated by administration of an effective amount of at least one compound which potentiates neurotrophin activity.

BRIEF DESCRIPTION OF THE DRAWINGS

The invention may be better understood with reference to the accompanying drawings, in which.

DETAILED DESCRIPTION OF THE INVENTION

The role of neurotrophic factors in development and adult function of neurons of the mammalian brain, in particular of cholinergic and dopaminergic neurons which degenerate in human neurodegenerative diseases, has been the subject of considerable research. In the course of research, it was first determined that K-252a and K-252b inhibit NGF mediated actions on cholinergic neurons in cell culture. Both compounds at relatively high dosages were found to completely and selectively prevent the trophic action of NGF on these cells, as reflected by an increase in the activity of the cholinergic marker enzyme choline acetyltransferase (ChAT).

In addition to the inhibitory effects observed at higher dosages, it has now surprisingly been determined that compounds of general formula I, such as K-252a and K-252b, also potentiate the activity of neurotrophins in a heretofore unobserved manner. This discovery makes possible not only a more comprehensive understanding of the molecular mechanisms of neurotrophin action, but also a therapeutic potentiation of neurotrophin action using compositions which may be administered via conventional routes for low-molecular-weight therapeutic agents. In addition, the recognition that neurotrophin activity may be potentiated by administration of a non-peptide active agent enables the development of a hitherto unanticipated realm of neuropharmacology.

Pursuant to one aspect of the present invention, there is provided a composition for potentiating neurotrophin action comprising an effective amount of at least one K-252 compound. By K-252 compound is meant both the heretofore identified metabolites K-252a and K-252b, and the derivatives thereof described in, e.g., U.S. Pat. Nos. 4,923,986 and 4,877,776.

A preferred class of K-252 compounds is represented by general formula I wherein:
$R^1$ and $R^3$ are independently selected from the group consisting of hydrogen, lower alkyl, hydroxy, lower alkoxy, halogen and —$NR^5R^6$ in which each of $R^5$ or $R^6$ is independently hydrogen, lower alkyl, carbamoyl or lower alkylaminocarbonyl;

$R^2$ is hydrogen or amino;

$R^4$ is hydrogen, halogen, carbamoyl, lower alkyl, amino or —$CH_2CH_2R^7$, in which $R^7$ is halogen, amino, di-lower alkylamino, hydroxy or hydroxy-substituted lower alkylamino;

one of $W^1$ and $W_2$ is hydrogen and the other is selected from the group consisting of hydrogen, hydroxy, lower alkoxy and lower alkylthio, or both $W^1$ and $W_2$ are combined together to represent oxygen;

X is hydrogen, —COOH, lower alkoxycarbonyl, in which $R^8$ and $R^9$ are independently hydrogen, lower alkyl or hydroxysubstituted lower alkyl, or $R^8$ is hydrogen and $R^9$ is hydroxy, —$CH_2A$ in which A is hydroxy, azido, lower alkylthio, lower alkylsulfenyl, or:

wherein $R^{10}$ and $R^{11}$ are independently selected from the group consisting of hydrogen, lower alkyl, allyl, carboxylic acid-substituted lower alkyl, dihydroxy-substituted lower alkyl, a residue of an α-amino acid in which the hydroxy of the carboxylic acid is removed and lower alkoxycarbonylsubstituted lower alkyl, or $R^{10}$ and $R^{11}$ are combined together to form —$CH_2CH_2$—B-$CH_2CH_2$— in which B is —$CH_2$—, —NH—, —S— or —O, —N=CH—$NR_2$ (wherein R is lower alkyl), —O—$COCH_2CH_2CO_2H$, or —C=N-$R^{12}$ in which $R^{12}$ is hydroxy, amino, guanidino or 2-imidazolylamino; and Y is hydroxy, lower alkoxy, or carbamoyloxy; or X and Y are combined together to form, as —X—Y—, O=, —CH$_2$O, —CH$_2$OCOO, —CH$_2$O—CS—O—, —CH$_2$—NR$^{13}$—CO—O— in which R$^{13}$ is hydrogen, lower alkyl, allyl, formylmethyl, —CH$_2$CH(OH)—CH$_2$OH or —CH$_2$CH=N—NHC(NH$_2$)=NH, —CH$_2$—NH—CS—O—, —CH$_2$—O—SO—O— or:

wherein R$^{14}$ is lower alkyl or lower alkylthio.

This preferred class of compounds embraces K-252 compounds as described in, e.g., the aforementioned U.S. Pat. Nos. 4,923,986 and 4,877,776, as well as the naturally-occurring K-252 compounds.

In the foregoing definitions, lower alkyl includes both straight-chain and branched alkyl having 1 to 5 carbon atoms, and halogen includes bromine, chlorine, fluorine and iodine. As would be readily apparent to those skilled in the art, general formula I embraces K-252a, K-252b and derivatives thereof as described in the aforementioned U.S. Pat. Nos. 4,877,776 and 4,923,986. Detailed methods for the preparation of the compounds of general formula I are provided in U.S. Pat. Nos. 4,877,776 and 4,923,986, and a large number of these compounds are concretely exemplified therein. Through routine implementation of the synthetic methods disclosed in U.S. Pat. Nos. 4,923,986 and 4,877,776 and other standard techniques, a wide variety of K-252 compounds may be prepared for evaluation of specificity in neurotrophin potentiation activity. Particularly preferred compounds of general formula I for use in particular in potentiating the action of NT-3 are those compounds in which W$_1$, W$_2$, R$^1$, R$^2$, R$^3$ and R$^4$ are all hydrogen, Y is OH and X is either —COOCH$_3$ (K-152a) or —COOH (K-252b).

K-252b was used for most further detailed investigations, as it was effective over a wide range of concentrations and lacked cytotoxicity. K-252b has now been demonstrated to exhibit a biphasic activity profile: It is both a selective inhibitor of growth factors of the neurotrophin family and, at lower concentrations, potentiates NT-3 actions. K-252b enhances the trophic activity of NT-3 on primary neurons and PC12 cells and also stimulates the NT-3 mediated tyrosine phosphorylation of trk and the trk substrate phospholipase C-gammal. The stimulatory actions of K-252b are believed due to direct or indirect effects of this compound on trk signal transduction pathways.

Compounds of general formula I (as exemplified by K-252b) selectively modify actions of the neurotrophin growth factor family. At nM concentrations, K-252b selectively potentiates the actions of NT-3; at µM concentrations, the compound inhibits the actions of all neurotrophins, without interfering with transduction mechanisms of non-neurotrophin growth factors. Furthermore, the selective inhibitory and stimulatory actions of K-252b on neurotrophins are likely due to a direct interaction with tyrosine protein kinase activity of trk-type receptor proteins.

A possible explanation for the observation of increased NT-3 effects is that K-252b modifies trk in a manner that this receptor interacts with NT-3, but not NGF, more efficiently. While K-252a does not interfere with binding of $^{125}$I-NGF to PC12 cells, it remains possible that the related K-252b might affect binding of selected neurotrophins to specific active sites. Such an effect could involve other proteins believed to be part of neurotrophin receptors, like the p75—NGFR low affinity NGF receptor protein.

K-252b, besides inhibiting trk protein kinase activity, interferes with protein kinase C, as well as cAMP- and cGMP-dependent protein kinases with K$_i$ values in the 10–100 nM range as shown by in vitro assay systems. Given this rather broad spectrum of inhibitory actions, the selective inhibition of neurotrophin effects is surprising. It seems possible that in intact cells K-252b interacts with extracellular or transmembranal domains of trk proteins, without access to intracellular protein kinases. This possibility is supported by recent findings showing that K-252b inhibits the protein kinase activity of the platelet-derived growth factor in cell-free preparations but not in intact cells.

While it is contemplated in accordance with the present invention that neurotrophin potentiating agents may be administered in conjunction with native and/or recombinant neurotrophins themselves in a manner as previously described herein, the discovery of neurotrophin potentiating agents (such as the low-molecular-weight compounds of general formula I) provide the significant advantage relative to the neurotrophic peptides themselves that they may be administered alone by the wide variety of routes heretofore employed for administration of non-peptide active agents in order to potentiate the activity of the patient's own neurotrophic factors. For example, oral, intravenous, subcutaneous, intramuscular, mucosal and transdermal routes of administration all would be suitable for use in accordance with the present invention.

In view of the biphasic activity profile of the compounds of general formula I, it is important that the compounds be provided in a amount effective to achieve the desired neurotrophin potentiation but less than the amount which results in the inhibitory activity. An effective dose in vitro for these purposes is in the range of about 0.1–10 nM (approximately 44.1–4,410 ng/l). Therefore, assuming uniform distribution in the human body and an average human body size of 70 kg (i.e., 70 liters), a dose projection of approximately 3–300 µg is obtained. Of course, based upon the foregoing information, it would be well within the skill of those working in the pharmaceutical field to determine the optimum dosage for any given compound of general formula I in any particular context.

In addition to the traditional routes of administration which have been practiced for centuries in the medical arts (e.g., oral and intravenous administration), more recently-developed techniques for administration of the compounds of general formula I may be employed. For transdermal delivery of the active agents, suitable pads or bandages are well known in the art. Typically, these pads comprise a backing member defining one exterior surface, a surface of pressure-sensitive adhesive defining a second exterior surface, and disposed therebetween a reservoir containing the active agents confined therein. Suitable transdermal delivery systems are disclosed in U.S. Pat. Nos. 3,731,683 and 3,797,494 to Zaffaroni and U.S. Pat. No. 4,336,243 to Sanvordeker et al., the entire disclosures of which are hereby incorporated by reference.

Other suitable formulations would also be readily apparent to those of skill in the art. For example, administration may be effected subcutaneously or intramuscularly with slowly-dissolving pellets of crystalline or microcrystalline materials, or directly as a crystalline or microcrystalline aqueous suspension. In addition to the compounds of general formula I, pharmacologically acceptable salts thereof are also contemplated for use in accordance with the present invention. As indicated in U.S. Pat. No. 4,923,986, in cases where the compound of general formula I is an acidic compound, base addition salts can be formed; where the compound of general formula I is basic, acid addition salts can be formed. Suitable base and acid addition salts for use in pharmaceutical preparations are well known to those skilled in the art, and illustrative examples thereof are described in the aforementioned U.S. Pat. No. 4,923,986.

Compounds of general formula I, such as K-252b, are also unique tools to study the mechanisms of action of neurotrophins and to demonstrate biological actions of these proteins in vivo and in vitro. Compared to the related compounds K-252a and staurosporine, which show complex patterns of activity and are cytotoxic, K-252b is a non-toxic and highly selective modifier of neurotrophin actions in vitro.

The following examples will serve to illustrate the invention without in any way being limiting thereon.

EXAMPLES

The preparations of human recombinant neurotrophins were produced in a Chinese hamster ovary cell line according to a published procedure [Knusel, B. et al., "Trophic actions of recombinant human nerve growth factor on cultured rat embryonic CNS cells," *Experimental Neurology* 110:274–383 (1990)]. The neurotrophins were purified to >95% purity using chromatographic procedures. The neurotrophins were initially contained at a concentration of 0.2–1 mg/ml at pH 3 and were further diluted in culture medium immediately before use. Biological activity for all tested neurotrophin preparations was determined with chick dorsal root ganglion and nodose ganglion assays. Recombinant human des(1–3)-insulin-like growth factor-1 (des-IGF-1) was obtained from Genentech, South San Francisco, Calif. and initially contained in 100 mM sodium acetate.

K-252b was obtained from Kyowa Hakko Kogyo Co., Tokyo, Japan. K-252a, KT5720, KT5823, KT5296 and staurosporine were obtained from Kamiya Biomedical Company (Thousand Oaks, Calif.). These compounds were dissolved in dimethyl sulfoxide (DMSO) at 2 mM concentrations. Aliquots of this solution were kept at −70° C. Maximal concentration of DMSO in the medium was 0.01%, which was found not to affect the cultures.

Example 1
Inhibitory activity of K-252b

Recombinant human NGF (rhNGF), BDNF (rhBDNF), and NT-3 (rhNT-3) and K-252b were added to primary cultures of fetal rat brain neurons containing either forebrain cholinergic or midbrain dopaminergic neurons. A broad range of concentrations of K-252b were tested in presence of 50 ng/ml rhNGF, 200 ng/ml rhBDNF and 1 μg/ml rhNT-3, growth factor concentrations producing maximal trophic actions on cholinergic neurons. The trophic action was monitored by measuring the activity of ChAT, a parameter reflecting both survival and transmitter-specific differentiation of cholinergic cells.

Primary cultures of fetal rat brain septal and mesencephalic cells were prepared in a heretofore known manner [Knusel et al., supra]. Briefly, defined areas were dissected from fetal rat brains (Wistar, E15–16, Charles River, Mass.). The septal area contained the cholinergic neurons from septum, diagonal band of Broca and nucleus basalis. The ventral mesencephalon containing the dopaminergic neurons of the substantia nigra and the ventral tegmental area was dissected and dissociated mechanically. The cells were plated in 16 mm multiwell plates precoated with polyethyleneimine (1 mg/ml, 37° C., overnight), containing 0.5 ml modified L-15 medium supplemented with 5% heat inactivated horse serum and 0.5% heat inactivated fetal calf serum. Modified L-15 was prepared [Knusel et al., "Selective and Nonselective Stimulation of Central Cholinergic and dopaminergic Development in vitro by Nerve Growth Factor, Basic Fibroblast Growth Factor, Epidermal Growth Factor, Insulin and the Insulin-like Growth Factors I and II," *J. Neurosci.* 10:558–570 (1990)] by adding various amino acids, vitamins, antibiotics, glucose and $NaHCO_3$ to Leibovitz's L-15 medium (Gibco, Grand Island, N.Y.). Plating densities were $4\times10^5$ cells/cm$^2$ for basal forebrain cultures and $3\times10^5$ cells/cm$^2$ for mesencephalic cultures. Of these cells, 0.5 to 1% were cholinergic or dopaminergic, respectively. Growth factors were typically added on the second day of culture and the cells were grown for 5 or more days. For ChAT assays tissue was homogenized in 250 μl of 50 mM Tris-HCl buffer, pH 6.0 with 0.3% Triton X-100. [1–$^{14}$C]acetylcoenzyme A (NEN) concentration was 20 μM and specific activity 4.09 Ci/mol. To measure dopamine uptake, cultures were preincubated for 5 min at 37° C. with 250 μl incubation solution (5 mM glucose, 1 mM ascorbic acid in PBS) containing 1 mM pargyline. [$^3$H]dopamine (37 Ci/mmol) was then added to give a final concentration of 50 nM and the cultures were incubated for another 15 minutes. Blanks were obtained by incubating cells at 0° C.

Figure 1:
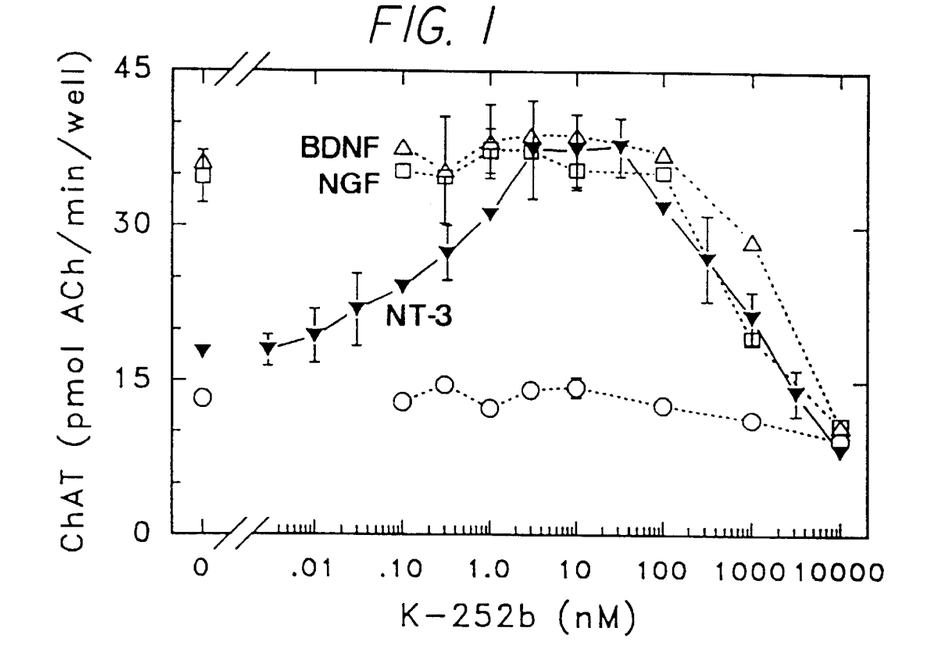
FIG. 1 illustrates the levels of ChAT activity in cultures of rat basal forebrain treated with recombinant human nerve growth factor (rhNGF), recombinant human brain-derived neurotrophic factor (rhBDNF), or recombinant human neurotrophin-3 (rhNT-3) and K-252b.

FIG. 1 illustrates levels of ChAT activity in cultures of rat basal forebrain treated with rhNGF, rhBDNF, or rhNT- and K-252b. Growth factors were added on the second day of culture and the cells were grown for 5 days. Growth factor concentrations producing maximal elevations of ChAT activity were used. In FIG. 1, ○ represents the control; □, 50 ng/ml rhNGF; Δ, 200 ng/ml rhBDNF; and ▼, 1 μg/ml rhNT-3. The ChAT stimulation mediated by all three neurotrophins was inhibited by K-252b at concentrations above 200 nM. At concentrations between 100 pM and 30 nM, K-252b potentiated the actions of NT-3 without affecting those of NGF or BDNF. N=4 per data point. Error bars represent SEMs and were omitted where they would have appeared smaller than the symbol.

K-252b, at concentrations higher than 200 nM, inhibited the ChAT activity increase mediated by all three neurotrophins (FIG. 1). The concentration requirements for the inhibitions of rhNGF, rhBDNF and rhNT-3 actions appeared identical. The minimal concentration of K-252b which was required to completely abolish the responses was approximately 2 μM (FIG. 1). The increases in CHAT activity mediated by basic fibroblast growth factor (bFGF), insulin, and insulin-like growth factor-1 were not affected by K-252b.

BDNF, but not NGF or NT-3, trophically acts on dopaminergic neurons as reflected by an increase in the activity of dopamine uptake by these cells. Similar to its actions on cholinergic neurons, K-252b prevented the increase in dopamine uptake mediated by BDNF, as shown in Table 1. Dopamine uptake is also stimulated by other growth factors, including bFGF, epidermal growth factor, insulin, insulin-like growth factors-1 and -2. K-252b does not inhibit the stimulatory action of bFGF and insulin. As a additional control, des-IGF-1 was used; K-252b was found not to inhibit its stimulatory action on dopamine uptake (Table 1). The findings obtained on central cholinergic and dopaminergic neurons showed that K-252b, at concentrations above 200 nM, completely and selectively blocks the actions of all neurotrophins stimulating these cells in primary cultures, whereas comparable effects of non-neurotrophin growth factors are not inhibited.

As shown in Table 1, K-252b inhibits the stimulatory action of rhBDNF, but not des-IGF-1 on dopamine uptake in cultures of ventral mesencephalon. In Table 1, dopamine uptake is given as fmol/min/culture dish. Cultures were grown in 24-well plates for 7 days in L-15 medium with 5% horse and 0.5% fetal bovine serum and treated with growth factors and K-252b from the second day of culture. rhBDNF, 200 ng/ml; des-IGF-1, 1 μg/ml; n=4; *different from respective control group, p <0.01 (Student's t-test). The apparent difference between control cultures grown in presence and absence of K-252b was statistically not significant. The experiment shown is a representative case of a total of 5 independent experiments.

TABLE 1

| Growth Factor Treatment | No K-252b Mean ± SEM | % of Control | With K-252b (5 μM) Mean ± SEM | % of Control |
|---|---|---|---|---|
| Control | 15.3 ± 3.6 | | 11.4 ± 0.2 | |
| rhBDNF | 28.0 ± 0.3* | 183 | 13.6 ± 0.7 | 119 |
| des-IGF-1 | 26.3 ± 1.1* | 172 | 22.9 ± 1.0* | 201 |

Example 2
Potentiation of NT-3 actions by K-252b on brain neurons

Surprisingly, the detailed dose-response analysis of K-252b actions on cholinergic neurons revealed that the compound strongly enhanced the trophic effect of NT-3 on these cells at concentrations lower than those producing inhibitory effects. In the presence of 10–100 nM of K-252b, NT-3 (which by itself elevated ChAT activity only by approximately 20% of the NGF-induced elevation) produced the same stimulatory effect as NGF (FIG. 1). The stimulatory effects of NGF or BDNF on cholinergic neurons were not potentiated by these low concentrations of K-252b (FIG. 1), and similarly the low concentrations did not potentiate the action of BDNF on dopaminergic neurons.

Figure 2:
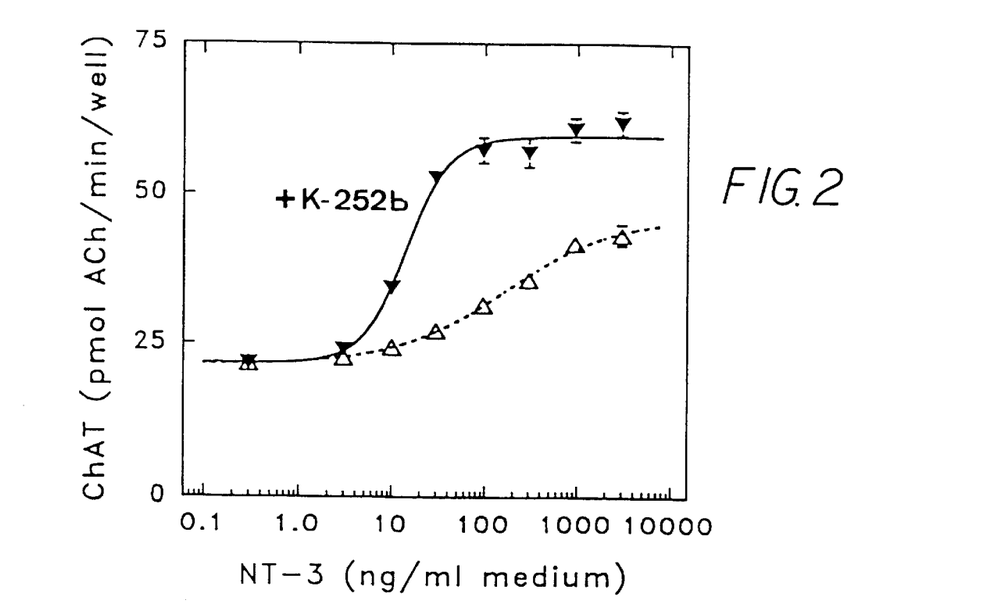
FIG. 2 illustrates increases in potency and efficacy of NT-3 stimulation of ChAT activity in cultures of rat basal forebrain upon addition of 50 nM K-252b.

The detailed dose-response analysis revealed that K-252b, at 50 nM, increased both potency and maximal efficacy of the trophic action of NT-3 (FIG. 2). 50 nM K-252b increased potency and efficacy of NT-3 stimulation of ChAT activity in cultures of rat basal forebrain. Half-maximal concentrations were calculated by non-linear fit of a sigmoid curve. The broken line represents NT-3 alone, $ED_{50}$=175±72.6 ng/ml (mean±S.E.); the solid line represents NT-3 +K-252b, $ED_{50}$=14.3±1.6 ng/ml; n=8 per symbol. Culture conditions were as described in connection with the results illustrated in FIG. 1.

Example 3
Potentiation of neurite NT-3 mediated survival of chick sensory neurons and neurite outgrowth of PC12 cells To establish generally that K-252b (at concentrations lower than those inhibiting neurotrophin responses) acts as a selective enhancer of NT-3, cultures of different neurotrophin responsive cell populations were tested. Survival and neurite outgrowth of chick dorsal root ganglia neurons (DRG) is supported by NGF, BDNF and NT-3, and the extent of the effect and the subpopulation supported by each factor is a function of the embryonic age of the animals used to prepare the cultures. In DRG cultures of embryonic day 9, NGF is most effective in promoting neuronal survival, whereas NT-3 only produces a moderate effect.

DRGs of embryonic day 9 chicks were dissected and dissociated using enzymatic and mechanical procedures as described in the literature [Rosenthal, A. et al., "Primary Structure and Biological Activity of a Novel Human Neurotrophic Factor," Neuron 4:767–773 (1990)]. 1800 neurons were plated per well in 96-well tissue culture plates pre-treated with polyornithine (500 μg/ml) and laminin (10 μg/ml). Cells were incubated for 48 hrs with or without growth factors and the indicated concentrations of K-252b. Phase-bright cells with elaborated neurites 5× the diameter of the cell bodies were then counted.

Figure 3:
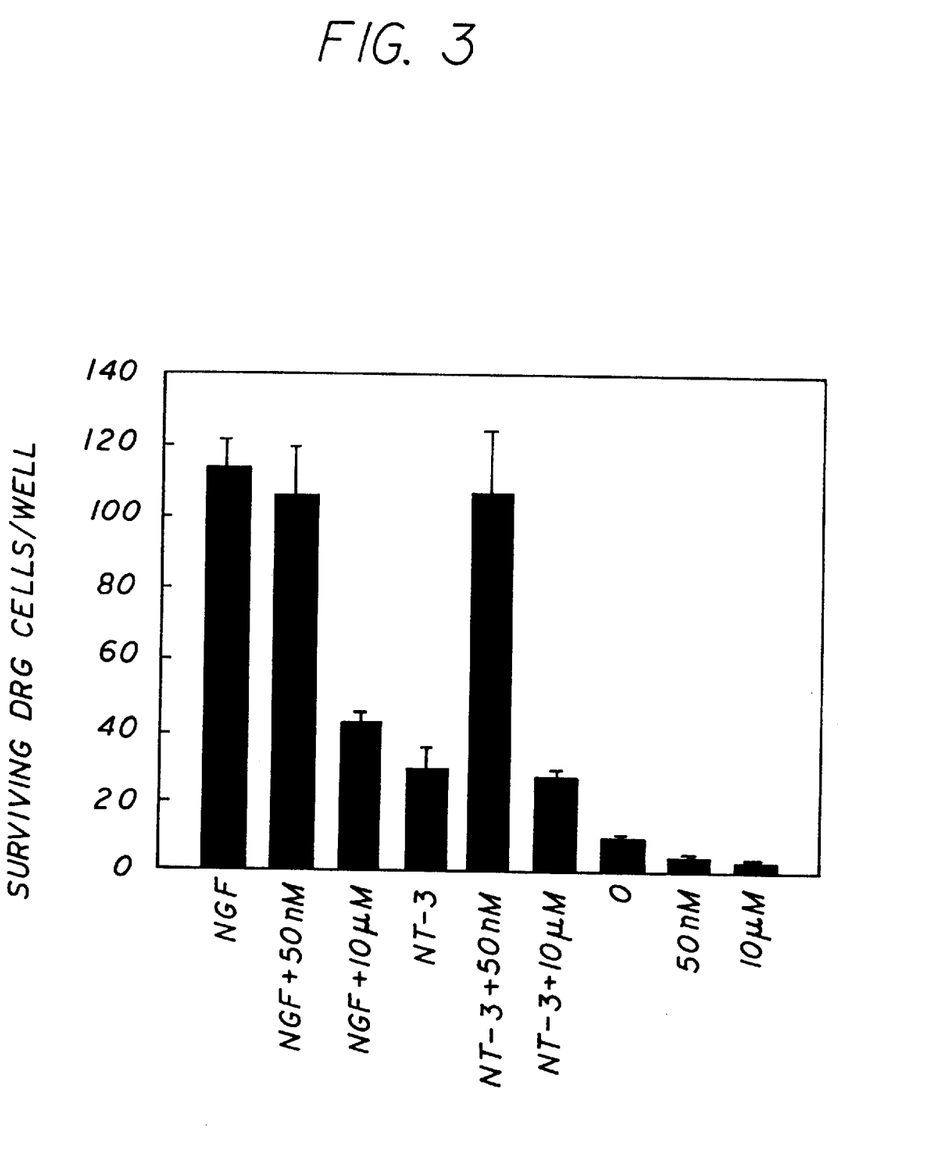
FIG. 3 illustrates levels of survival of dissociated chick DRG neurons in presence of rhNGF (100 ng/ml) or rhNT-3 (100 ng/ml) and K-252b.

Similar to the findings obtained in primary cultures of brain cholinergic neurons, low concentration of K-252b (50 nM) potentiated the survival promoting action of a maximally effective concentration of NT-3 (FIG. 3). Survival of dissociated chick DRG neurons in presence of rhNGF (100 ng/ml) or rhNT-3 (100 ng/ml) and K-252b is illustrated in FIG. 3; concentrations on the horizontal axis are for K-252b. The columns represent means +SEMs. The number of neurons supported by the combination of NT-3 and 50 nM K-252b was identical to that supported by NGF alone. The same concentration of K-252b failed to influence survival mediated by NGF (FIG. 3) or BDNF. High concentrations of K-252b (10 μM) inhibited the action of NGF on sensory neurons, as found for cholinergic neurons (FIG. 3). Similar results were also seen in cultures of dissociated chick sympathetic neurons.

PC12 cells were grown as described earlier [Kaplan et al., 1990, 1991a, b]. To assess effects on neurite outgrowth, cells were incubated for 48 hours with K-252b (50 nM) and NT-3 or NGF (50 ng/ml). Neurites were scored if they were a length of one cell body or more.

To measure the status of trk tyrosine phosphorylation, PC12 cells were lysed and immunoprecipitated with anti-trk serum. The trk proteins were subjected to 7.5% SDS-PAGE and analyzed by immunoblotting with anti-phosphotyrosine antibodies as described in detail in the literature [Kaplan, D. R. et al., "PDGF beta receptor stimulates tyrosine phosphorylation of GAP and association of GAP with a signaling complex," Cell 61:125–133 (1990)]. Tyrosine phosphorylation of cellular proteins was assayed by probing Western blots of lysates of PC12 cells incubated with K-252b and NT-3 or NGF with anti-phosphotyrosine antibodies. Phospholipase C gammal was identified in these blots as described elsewhere [Vetter, M.L. et al., "Nerve growth factor rapidly stimulates tyrosine phosphorylation of phospholipase C-gammal by a kinase activity associated with the product of trk protooncogene," Proc. Natl Acad. Sci. USA 88:5650–5654 (1991)].

Figure 4A:
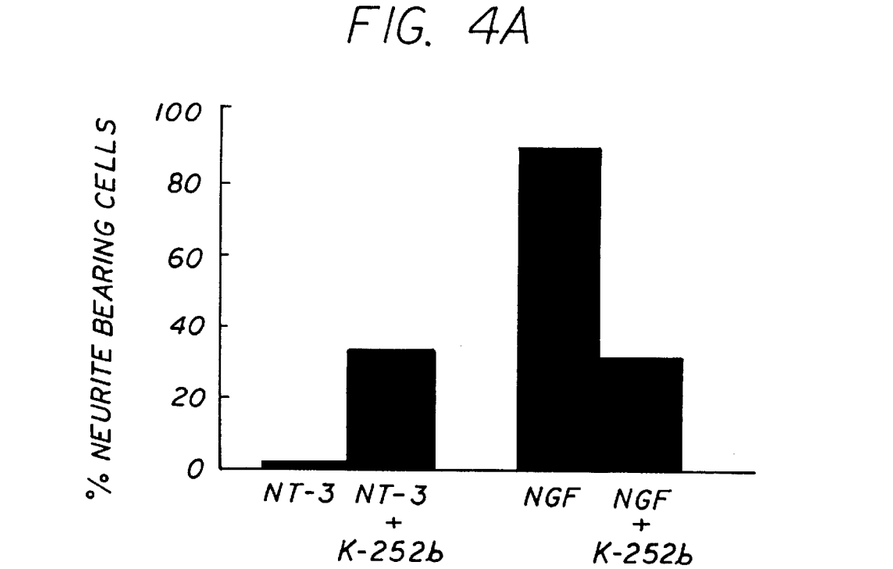
FIG. 4 illustrates stimulation of NT-3 induced neurite outgrowth and trk tyrosine phosphorylation in PC12 cells with inhibition of NGF induced effects upon treatment with K-252b.
Figure 4B:
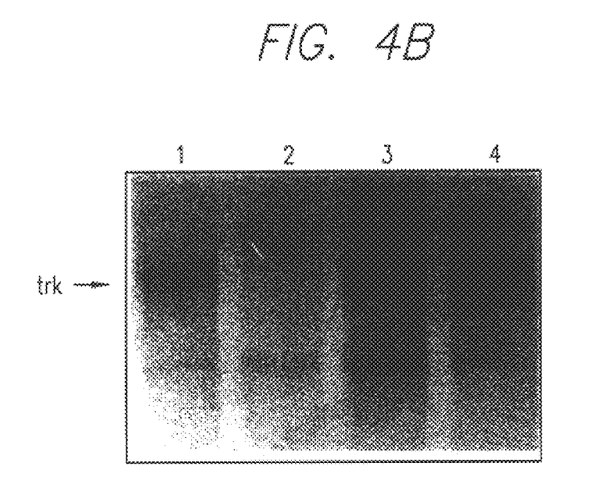

Experiments on PC12 cells confirmed observations made on primary neuron cultures. Treatment with K-252b stimulated NT-3 induced neurite outgrowth and trk tyrosine phosphorylation in PC12 cells while inhibiting NGF induced effects. PC12 cells were incubated for 48 hours with K-252b (50 nM) and NT-3 or NGF (50 ng/ml). FIG. 4A illustrates the % cells with neurites after 48 hours incubation. Neurites were scored if they were a length of one cell body or more. PC12 cells were subsequently lysed and immunoprecipitated with anti-trk serum. trk proteins were subjected to SDS-PAGE and analyzed by immunoblotting with anti-phosphotyrosine antibodies (FIG. 4B). Lane 1, NT-3 +K-252b; lane 2, NT-3; lane 3, NGF +K-252b; lane 4, NGF. For FIG. 4C, PC12 cells were incubated for 1 hour in K-252b (50 nM or 10 μM) and with NT-3 or NGF for 5 minutes prior to lysis; other methods were the same as described for FIG. 4B. Lane 1, NT-3+10 μM K-252b; lane 2, NT-3±50 nM K-252b; lane 3, NT-3; lane 4, NGF+10 μM K-252b; lane 5, NGF+50 nM K-252b; lane 6, NGF; lane 7, untreated control.

PC12 cells incubated for 48 hours in the presence of NT-3 (50 ng/ml) and K-252b (50 nM) showed significantly more neurite outgrowth activity than cells incubated with NT-3 alone (FIG. 4A). At the concentration of K-252b used in this experiment, NGF-induced neurite outgrowth was reduced approximately three-fold, whereas in the primary neuron cultures no significant inhibition was detected at this concentration (FIG. 1).

Example 4
Effects of K-252b on tyrosine phosphorylation of trk

Figure 4C:
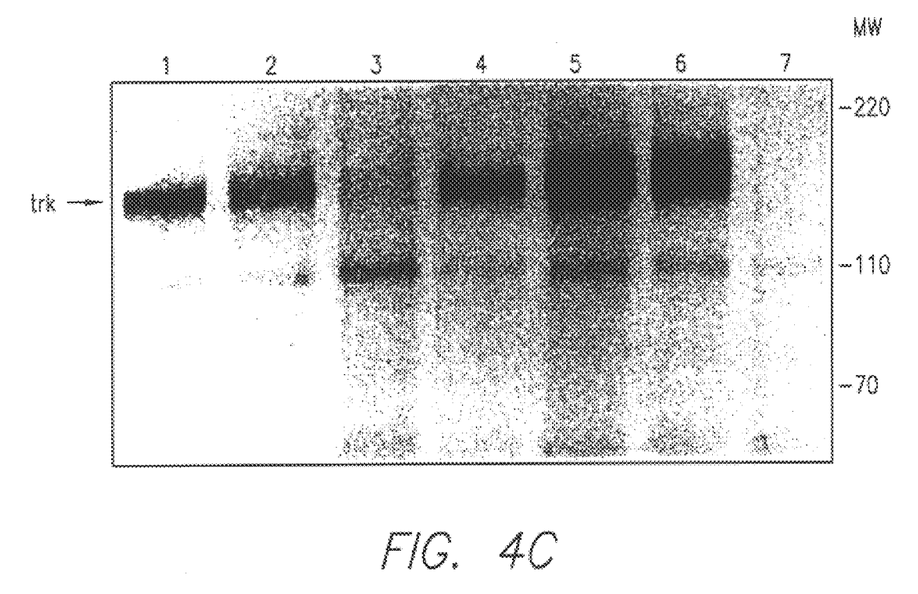

The fact that K-252b inhibits various protein kinases in cell free systems and the recent discovery that trk proto-oncogenes are involved in the formation of high affinity neurotrophin receptors suggested that K-252b exerts its neurotrophin inhibitory and stimulatory actions by directly interfering with protein kinases of the trk protein family. NGF has been shown to stimulate the tyrosine phosphorylation of p140 trk within minutes of addition to PC12 cells. NT-3 induces only low levels of trk tyrosine phosphorylation and neurite outgrowth in these cells (FIG. 4A). PC12 cells which were exposed to NT-3 or NGF for 48 hours in the presence or absence of K-252b (FIG. 4A) were also analyzed for p140 trk tyrosine phosphorylation (FIG. 4B). NGF strongly stimulated trk tyrosine phosphorylation whereas no phosphorylation was detectable with NT-3 alone. However, a clear increase in trk tyrosine phosphorylation was seen in cells grown in presence of NT-3 and 50 nM K-252b (FIG. 4B). Similar effects were observed when cells were acutely treated for 1 hour with K-252b followed by 5 minutes NT-3 (FIG. 4C). Stimulation of tyrosine phosphorylation by NT-3 alone was minimal but was greatly enhanced by the simultaneous presence of K-252b. NGF produced a pronounced increase of trk phosphorylation and K-252b at 10 μM partially inhibited this effect. Cells treated with the inhibitor alone and without NT-3 were identical to untreated controls. In contrast to the pronounced effects of K-252b on trk tyrosine phosphorylation mediated by neurotrophins, K-252b failed to influence similar responses induced by epidermal growth factor and basic fibroblast growth factor on their corresponding receptors.

Tyrosine phosphorylation of cellular proteins was examined in PC12 cells treated with NT-3 or NGF in presence of K-252b. The tyrosine phosphorylation of phospholipase C gamma-1, a direct target of the trk tyrosine kinase and several other cellular proteins was inhibited by K-252b in NGF treated cells. In contrast, the NT-3 mediated tyrosine phosphorylation of these proteins in PC12 cells was enhanced by 50 nM of K-252b.

Example 5

Human trk and trkB were expressed in Sf9 insect cells transfected using a baculovirus system. The trk proteins were immunoprecipitated as described above and the precipitates were incubated with 20 μCi [gamma-$^{32}$P]ATP, 10 mM MnCl$_2$, 20 mM Tris, pH 7.4, for 5 min at 25° C. in the presence of increasing amounts of K-252b or control solution. Phosphorylated proteins were analyzed as described for FIG. 4B. The tyrosine kinase activity of the trk and trkB proteins was activated in the absence of ligand, a common observation for receptor tyrosine kinase produced in the baculovirus system. The trk and trkB proteins were 25% pure as assayed by SDS-PAGE.

Figure 5:
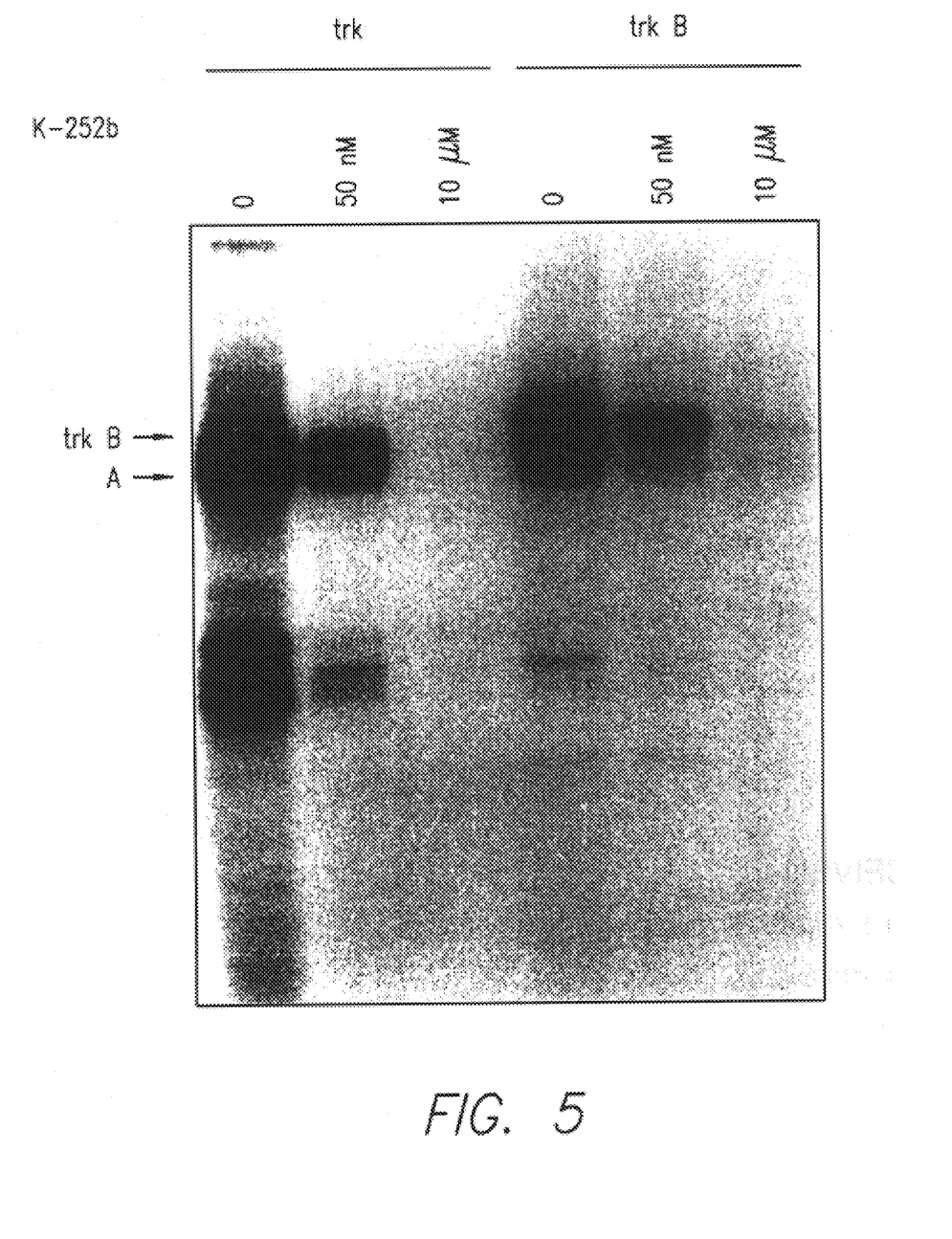
FIG. 5 illustrates direct interaction of K-252b with the trk and trkB protein.

A direct action of K-252b on trk was demonstrated using partially purified recombinant trk proteins. 10 μM K-252b completely prevented tyrosine phosphorylation of both, trk and trkB in a cell-free system (FIG. 5). K-252b interacts directly with the trk and trkB protein. Human trk and trkB were expressed in Sf9 insect cells transfected using a baculovirus system. trk proteins were immunoprecipitated and the precipitates were incubated with [gamma$^{32}$P]ATP in the presence of increasing amounts of K-252b or control solution.

Example 6
Structural Requirements for Potentiation Effect

To assess the structural features of the compounds of general formula I which are responsible for selective potentiation of NT-3 and to decide whether these features are different from the ones mediating neurotrophin inhibition, K252b and various structural relatives were studied. In addition to K-252b ("K2b"), K-252a ("K2a"), KT5720 ("K57"), KT5823 ("K58"), KT5296 ("K59") (within the scope of general formula I):

-continued

KT5296 and staurosporine ("Stau")

Staurosporine

Figure 6:
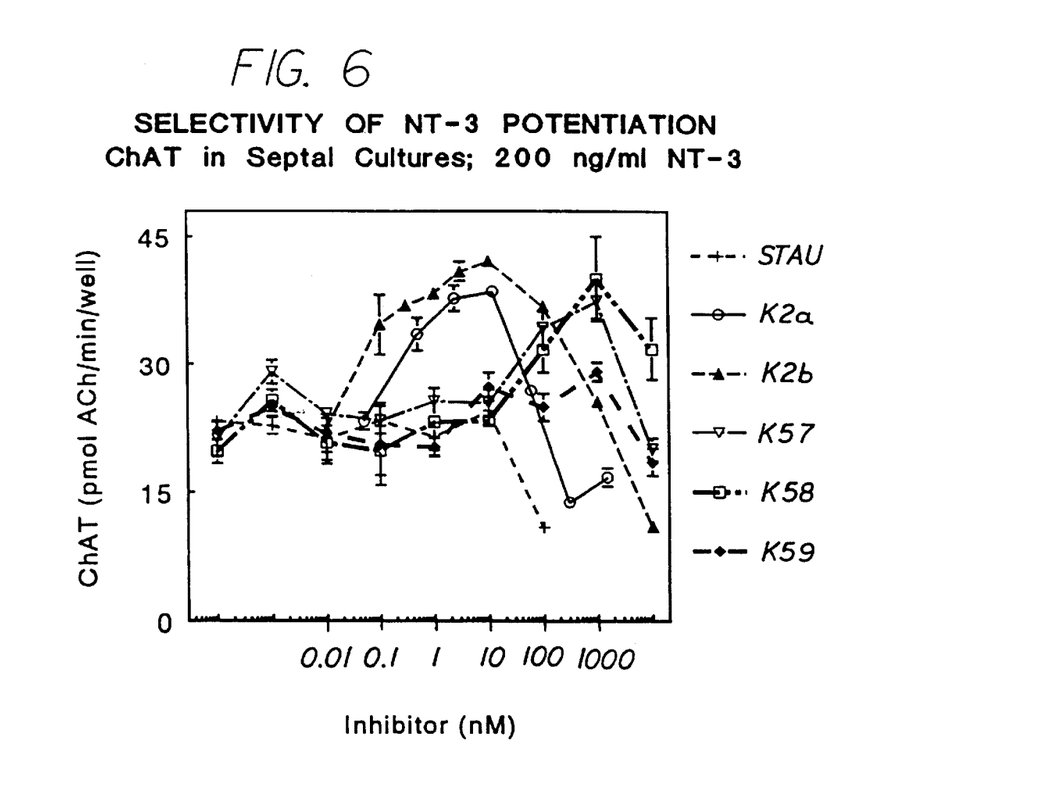
FIG. 6 illustrates the selective potentiation of NT-3 by K-252b and various structurally related compositions relative to a control composition.

(outside the scope of general formula I) were found to inhibit the action of central cholinergic neurons. These compounds were accordingly tested for possible NT-3 potentiation at lower concentrations than necessary for NGF inhibition. Culture conditions were as described in Example 1. Cultures were untreated (controls) or treated with 200 ng/ml NT-3 and increasing concentrations of the inhibitors. The findings are shown in FIG. 6, in which "Stau", "K2a", "K2b", "K57", "K58", "K59" represent, respectively, staurosporine, K-252a, K-252b, KT5720, KT5823, and KT5296. K-252a, KT5720 and KT5823 induced potentiation similar to K-252b. Staurosporine and KT5296 were ineffective. The absence of NT-3 potentiating effects of staurosporine and KT5296, which also selectively inhibit NGF, demonstrates that the structural requirements for NGF inhibition and for NT-3 potentiation are different from one another. Moreover, this result confirms that compounds of general formula I exhibit an unexpected activity relative to compounds of remarkably similar structure but lacking the characteristic five-membered oxygen-containing ring of general formula I. The studies furthermore revealed that addition of hydroxypropyl substituent in the aromatic ring system results in loss of the potentiating property.

While there have been shown and described the fundamental novel features of the invention, it will be understood that various omissions, substitutions and changes in the form and details of the invention illustrated may be made by those skilled in the art without departing from the spirit of the invention. It is the intention, therefore, to be limited only as indicated by the scope of the following claims.

What is claimed is:

1. A method for potentiating NT-3 activity in NT-3 responsive mammalian cells, the method comprising administering to said mammal an effective amount of a composition, said composition comprising at least one K-252 compound, said effective amount being sufficient to potentiate NT-3 activity but below an amount sufficient to inhibit neurotrophin activity.

2. A composition according to claim 1, wherein said K-252 compound has the formula:

wherein:
R$^1$ and R$^3$ are independently selected from the group consisting of hydrogen, lower alkyl, hydroxy, lower alkoxy, halogen and —NR$^5$R$^6$ in which each of R$^5$ or R$^6$ is independently hydrogen, lower alkyl, carbamoyl or lower alkylaminocarbonyl;

R$^2$ is hydrogen or amino;

R$^4$ is hydrogen, halogen, carbamoyl, lower alkyl, amino or —CH$_2$CH$_2$R$^7$, in which R$^7$ is halogen, amino, di-lower alkylamino, hydroxy or hydroxy-substituted lower alkylamino;

one of W$^1$ and W$_2$ is hydrogen and the other is selected from the group consisting of hydrogen, hydroxy, lower alkoxy and lower alkylthio, or both W$^1$ and W$_2$ are combined together to represent oxygen;

X is hydrogen, —COOH, lower alkoxycarbonyl, in which R$^8$ and R$^9$ are independently hydrogen, lower alkyl or hydroxysubstituted lower alkyl, or R$^8$ is hydrogen and R$^9$ is hydroxy, —CH$_2$A in which A is hydroxy, azido, lower alkylthio, lower alkylsulfenyl, or wherein R$^{10}$ and R$^{11}$ are independently selected from the group consisting of hydrogen, lower alkyl, allyl, carboxylic acid-substituted lower alkyl, dihydroxy-substituted lower alkyl, a residue of an α-amino acid in which the hydroxy of the carboxylic acid is removed and lower alkoxycarbonyl-substituted lower alkyl, or R$^{10}$ and R$^{11}$ are combined together to form —CH$_2$CH$_2$—B—CH$_2$CH$_2$— in which B is —CH$_2$—, —NH—, —S— or —O, —N=CH-NR$_2$ wherein R is lower alkyl, —O—COCH$_2$CH$_2$CO$_2$H, or —C=N—R$^{12}$ in which R$^{12}$ is hydroxy, amino, guanidino or 2-imidazolylamino; and Y is hydroxy, lower alkoxy, or carbamoyloxy; or X and Y are combined together to form, as —X—Y—, O=, —CH₂—O, —CH₂OCOO, —CH₂—O—CS—O—, —CH₂—NR¹³—CO—O— in which R¹³ is hydrogen, lower alkyl, allyl, formylmethyl, —CH₂CH(OH)—CH₂OH or —CH₂CH=N—NHC(NH₂)=NH, —CH₂—NH—CS—O—, —CH₂—O—SO—O— or wherein R¹⁴ is lower alkyl or lower alkylthio.

3. A method according to claim 2, wherein W₁, W₂, R¹, R², and R³ [and R⁴] are hydrogen, R⁴ is hydrogen or methyl, Y is OH or methoxy, and X is COOR¹⁵, wherein R¹⁵ is hydrogen or alkyl of 1–6 carbons.

4. A method according to claim 1, wherein said K-252 compound is K-252a or K-252b.

5. A method according to claim 4, wherein said effective amount provides a concentration of K-252 compound in mammalian body tissues in the range of about 0.1 nM to about 10 nM.

6. The method of claim 1, further comprising contacting said cells with neurotrophin.

7. A method for potentiating NT-3 activity in neurotrophin responsive cells, comprising contacting said cells with an effective amount of a K-252 compound, said effective amount being sufficient to potentiate NT-3 activity, but insufficient to inhibit NT-3 activity, wherein said K-252 compound is selected from the group consisting of K-252a, K-252b, KT5720, and KT5823.

8. A method according to claim 7, wherein said NT-3 activity potentiated comprises increased neuronal survival or neurite outgrowth.

9. A method according to claim 7, wherein said NT-3 activity potentiated comprises increased ChAT activity, trk tyrosine phosphorylation, or trk-mediated tyrosine phosphorylation of cellular proteins.

10. The method of claim 6, wherein said neurotrophin is NT-3.

* * * * *